(12) United States Patent
Carette et al.

(10) Patent No.: US 9,517,105 B2
(45) Date of Patent: Dec. 13, 2016

(54) MOVABLE HOLDER FOR MEDICAL INSTRUMENTS AND ASSOCIATED METHODS

(71) Applicant: Symmetry Medical Manufacturing, Inc., Warsaw, IN (US)

(72) Inventors: Brian Carette, Manchester, NH (US); George P. Hannafin, Hudson, NH (US)

(73) Assignee: Symmetry Medical Manufacturing, Inc., Warsaw, IN (US)

(*) Notice: Subject to any disclaimer, the term of this patent is extended or adjusted under 35 U.S.C. 154(b) by 42 days.

(21) Appl. No.: 14/722,779

(22) Filed: May 27, 2015

(65) Prior Publication Data

US 2015/0250545 A1 Sep. 10, 2015

Related U.S. Application Data

(62) Division of application No. 14/052,199, filed on Oct. 11, 2013, now Pat. No. 9,259,273.

(60) Provisional application No. 61/714,505, filed on Oct. 16, 2012.

(51) Int. Cl.

| *A61B 19/02* | (2006.01) |
|---|---|
| *A61L 2/26* | (2006.01) |
| *F16M 13/02* | (2006.01) |
| *A61L 2/06* | (2006.01) |
| *A61B 19/00* | (2006.01) |
| *A61C 19/00* | (2006.01) |

(52) U.S. Cl.
CPC ....... *A61B 19/0256* (2013.01); *A61B 19/0271* (2013.01); *A61L 2/06* (2013.01); *A61L 2/26* (2013.01); *F16M 13/02* (2013.01); *A61B 2019/267* (2013.01); *A61C 19/00* (2013.01); *A61C 19/002* (2013.01); *A61L 2202/24* (2013.01); *Y10T 29/4984* (2015.01); *Y10T 29/49826* (2015.01)

(58) Field of Classification Search
CPC ... A61B 19/0256; A61B 19/0271; A61L 2/06; A61L 2/26; F16M 13/02
See application file for complete search history.

(56) References Cited

U.S. PATENT DOCUMENTS

| 4,336,962 A * | 6/1982 | Read | B66C 1/442 |
| | | | 294/106 |
| 5,813,814 A * | 9/1998 | Smart | A01D 90/08 |
| | | | 414/111 |
| 2005/0015956 A1* | 1/2005 | Haws | B31B 19/90 |
| | | | 29/409 |
| 2013/0182381 A1* | 7/2013 | Gray | F16M 13/02 |
| | | | 361/679.01 |

* cited by examiner

*Primary Examiner* — Regina M Yoo
(74) *Attorney, Agent, or Firm* — Hayes Soloway, P.C.

(57) ABSTRACT

A movable instrument holding apparatus and method of retaining a medical instrument with a movable instrument holding apparatus are disclosed. The movable instrument holding apparatus includes a housing structure retaining a gripping structure. A rail is connected to the housing structure. A depressible arm is connected to the rail, the depressible arm having a first quantity of ratchet teeth, wherein the first quantity of ratchet teeth is movable with the depressible arm. A track is sized to receive the rail, wherein the track has a second quantity of ratchet teeth, and wherein the first quantity of ratchet teeth are engagable with the second quantity of ratchet teeth when the rail is positioned at least partially within the track.

3 Claims, 7 Drawing Sheets

MOVABLE HOLDER FOR MEDICAL INSTRUMENTS AND ASSOCIATED METHODS

CROSS REFERENCE TO RELATED APPLICATION

This application is a divisional of co-pending application Ser. No. 14/052,199, entitled "Movable Holder for Medical Instruments and Associated Methods" filed Oct. 11, 2013, the entire disclosure of which is incorporated herein by reference.

FIELD OF THE DISCLOSURE

The present disclosure is generally related to instrument holding devices and more particularly is related to a movable instrument holding apparatus and methods of using the same.

BACKGROUND OF THE DISCLOSURE

Within the medical industry, there is a need for holding a variety of medical instruments for various purposes. A surgeon needs to be able to access medical instruments for surgery quickly, a dentist needs to be able to access his or her dental tools, and virtually all medical instruments must be placed within a holder during a sterilization process. Conventional holding containers may include a variety of bases holding insertable trays that have specifically-designed areas for holding specific tools. However, with smaller tools, such as small dental tools, it is frequently inefficient to store them in these containers, since they're prone to being moved around and jostled as the container is moved. This may result in a grouping of smaller tools in one area, which means that the surgeon or medical staff member must sift through the grouping to locate a specific tool.

Conventionally, medical instruments are often held in containers or trays with holes and grommets. The grommets may be positioned within the hole and provide a secure interface between the medical instrument and the hole within the container or tray. Often, the grommets are sized to match a certain shaft size of a medical instrument, and a container or tray may include a variety of different sized grommets, each specifically engineered and designed to hold one of a variety of medical instruments. These medical instruments have varying shaft sizes and it often becomes tedious to search for the appropriately sized grommet that matches a particular shaft size of the medical instrument. It is not uncommon for a medical tray to have fifty or more grommets, with a dozen or more different sizes. Thus, the time it takes to match a specific medical instrument to a specifically sized grommet may result in inefficient use of valuable time.

Further, many medical instruments are not suited for sterilization while being held in a grommet, either because they lack the necessary shape to be retained within the grommet or because they do not become fully sterilized when placed in the grommet since the grommet hinders the ability for a sterilant to contact all portions of the medical instrument. For instruments of these types, it may be necessary to support them with fixtures that retain the instruments with less contact than conventional grommets. With the multitude of medical instruments that require sterilization, it may be inefficient for a medical worker to find an appropriate fixture that will work with a specific instrument.

Thus, a heretofore unaddressed need exists in the industry to address the aforementioned deficiencies and inadequacies.

SUMMARY OF THE DISCLOSURE

Embodiments of the present disclosure provide a movable instrument holding apparatus. Briefly described, in architecture, one embodiment of the apparatus, among others, can be implemented as follows. A housing structure is retaining a gripping structure. A rail is connected to the housing structure. A depressible arm is connected to the rail, the depressible arm having a first quantity of ratchet teeth, wherein the first quantity of ratchet teeth is movable with the depressible arm. A track is sized to receive the rail, wherein the track has a second quantity of ratchet teeth, and wherein the first quantity of ratchet teeth are engagable with the second quantity of ratchet teeth when the rail is positioned at least partially within the track.

The present disclosure can also be viewed as providing a method of retaining a medical instrument with a movable instrument holder. In this regard, one embodiment of such a method, among others, can be broadly summarized by the following steps: connecting a track to a medical instrument sterilization tray; positioning a rail within a channel formed in the track, wherein the rail is connected to a housing structure having at least one gripping structure supported therein; controlling engagement of the rail with the track with a depressible arm connected to the rail, wherein a first quantity of ratchet teeth formed on the depressible arm is engagable with a second quantity of ratchet teeth formed on the channel; and retaining the medical instrument between at least two of the gripping structures.

The present disclosure can also be viewed as providing a system of retaining a medical instrument. Briefly described, in architecture, one embodiment of the system, among others, can be implemented as follows. The system includes a plurality of housing structures, each of the plurality of housing structures retaining at least one gripping structure. A rail is connected to each of the housing structures. A depressible arm is connected to each of the rails, each of the depressible arms having a first quantity of ratchet teeth, wherein the first quantity of ratchet teeth is movable with the depressible arm, respectively. A length of track receives each of the rails within a channel formed within the length of track, wherein a second quantity of ratchet teeth is positioned along the channel, and wherein the first quantities of ratchet teeth are temporarily engaged with the second quantity of ratchet teeth.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
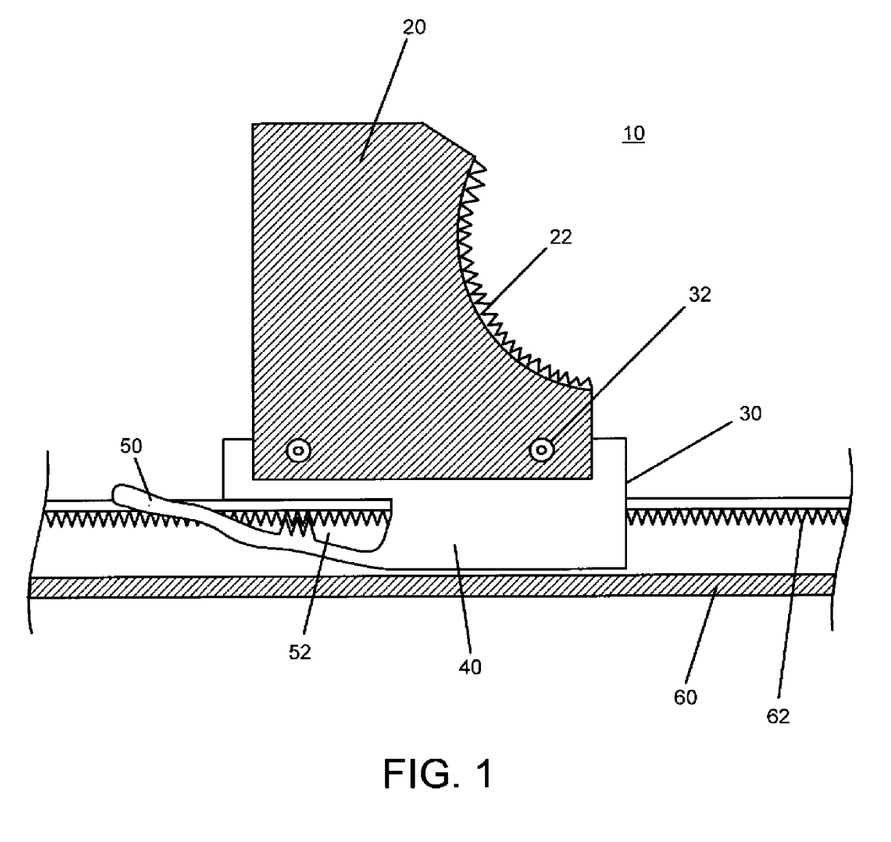
FIG. 1 is a side cross-sectional view illustration of a movable instrument holding apparatus, in accordance with a first exemplary embodiment of the present disclosure.

FIG. 1 is a side cross-sectional view illustration of a movable instrument holding apparatus 10, in accordance with a first exemplary embodiment of the present disclosure. The movable instrument holding apparatus 10, which may be referred to as 'apparatus 10,' includes housing structure 30 retaining a gripping structure 20. A rail 40 is connected with the housing structure 30. A depressible arm 50 is connected to the rail 40 and has a first quantity of ratchet teeth 52, wherein the first quantity of ratchet teeth 52 is movable with the depressible arm 50. A track 60 is sized to receive the rail 40, wherein the track 60 has a second quantity of ratchet teeth 62, and wherein the first quantity of ratchet teeth 52 are engagable with the second quantity of ratchet teeth 62 when the rail 40 is positioned at least partially within the track 60.

The apparatus 10 may be used for holding different types of instruments, namely medical instruments used for medical procedures, operations, and surgeries. For example, the apparatus 10 may be used to hold medical instruments in surgical environments before, during and/or after a surgical procedure, or a medical instrument sterilization process. Similarly, the apparatus 10 may be used with dental instruments for dental operations, routine cleanings, or for any other use. Other settings and uses within the medical field are also envisioned, all of which are considered within the scope of the present disclosure. The apparatus 10 is well suited for holding medical instruments during a sterilization process, where the medical instrument is contacted by sterilant or subjected to sterilizing conditions, such as high temperatures.

The apparatus 10 may contact and hold a medical instrument with the gripping structure 20. The gripping structure 20 may be formed from a resilient material, such as a silicone material with a high durometer, such that the gripping structure 20 can flex to hold a medical instrument successfully. However, the gripping structure 20 may also be formed from any number of other materials. The gripping structure 20 may have any shape, size or orientation, such as an arced structure with a plurality of small protrusions 22 which are suited for contact with the medical instrument. The small protrusions 22 may allow the medical instrument to be stationary retained, but still allow for sterilant to contact as much of the medical instrument as possible. The small protrusions 22 may be formed on the gripping structure 20 in any fashion, such as formed on a face of the gripping structure 20 that is shaped to receive the medical instrument. The gripping structure 20 may include a variety of dimensions, sizes, and shapes, including flat, angled, or pronged shapes, or any other shape not specifically mentions herein.

The gripping structure 20 is retained and supported by the housing structure 30, which may be formed from a hardened plastic or metal, or another material suitable for withstanding the conditions of a sterilization environment. The housing structure 30 may receive a portion of the gripping structure 20 therein, such as within a pocket or cavity of the housing structure 30, and secure the gripping structure 20 with fasteners 32, or similar structures. For example, the gripping structure 20 may be secured with fasteners 32 that are at least partially positioned within or through a portion of the gripping structures 20. In other examples, the gripping structure 20 may be frictionally, adhesively, or otherwise held on the housing structure 30. The gripping structure 20 may be removable or permanent within the housing structure 30, depending on the intended use of the apparatus 10. Furthermore, any number of independent or connected gripping structures 20 may be supported by a single housing structure 30.

The rail is formed with or attached to the housing structure 30. The rail 40 may commonly be integrally molded or machined with the housing structure 30 such that the two structures are substantially unitary. However, the rail 40 may also be formed separately from the housing structure 30 and later connected to it. The rail 40 may be positioned below the housing structure 30, such that the housing structure 30 is positioned between the rail 40 and the gripping structure 20. In this configuration, the rail 40 may interface with the track 60, thereby supporting the housing structure 30 and the gripping structure 20 above the track 60.

Figure 3:
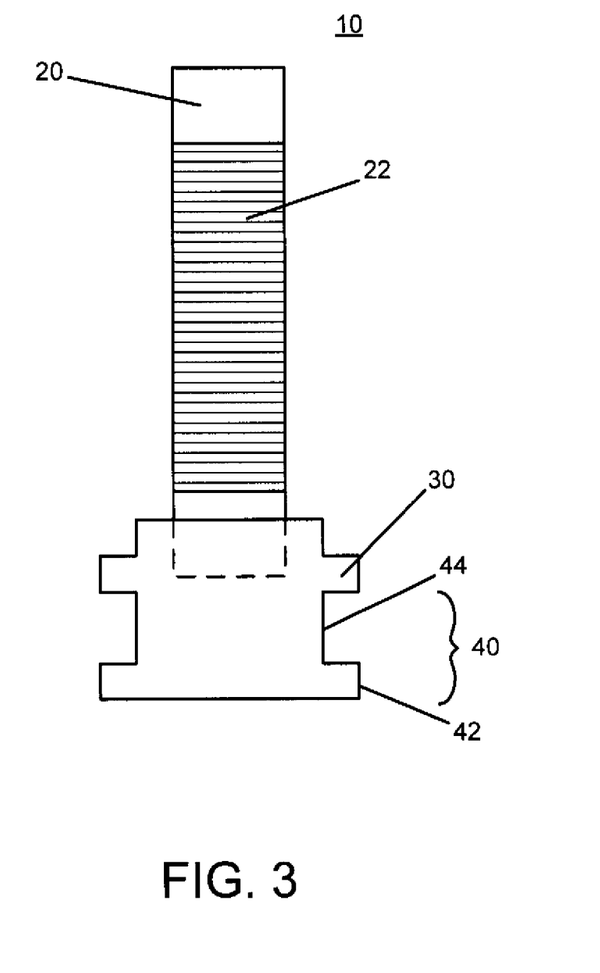
FIG. 3 is a front view illustration of the rail, housing structure, and gripping structure of the movable instrument holding apparatus of FIG. 1, in accordance with the first exemplary embodiment of the present disclosure.
Figure 5:
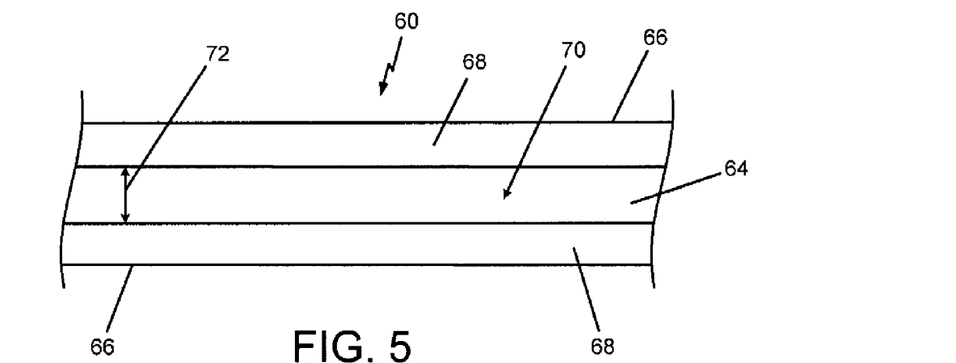
FIG. 5 is a top view illustration of the track of the movable instrument holding apparatus of FIG. 1, in accordance with the first exemplary embodiment of the present disclosure.
Figure 6:
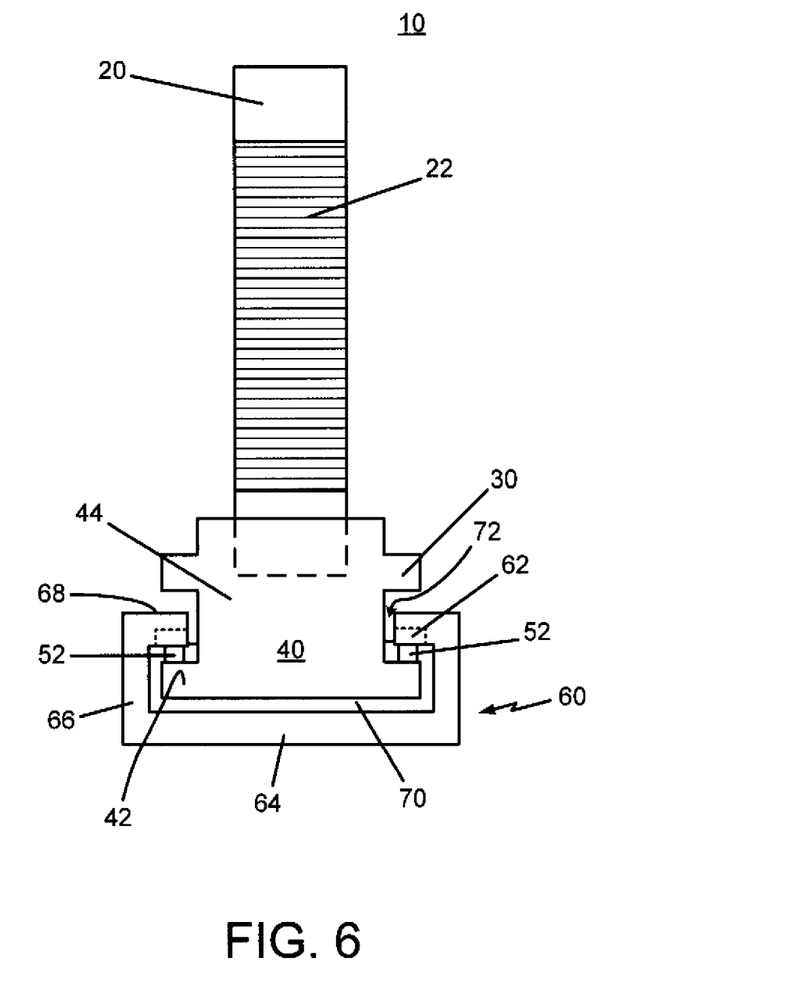
FIG. 6 is a front view illustration of the movable instrument holding apparatus of FIG. 1, in accordance with the first exemplary embodiment of the present disclosure.

The rail 40 may have a variety of shapes, including an inverted T shape, as is best shown in FIGS. 3 and 6. The shape of the rail 40 may be chosen to be compatible with the track 60, such that the two structures function together. The rail 40 may support the housing structure 30 and the gripping structure 20 when the rail 40 is positioned within the track 60, such that the gripping structure 20 can be used in any location along the track 60 that is needed. The track 60 may be shaped to receive the rail 40, as is best shown in FIG. 6. As is discussed further relative to FIGS. 4-6, the track 60 may have a base, sidewalls, and lips that allow for the rail 40 to be positioned therein but still be capable of supporting the housing structure 30 and the gripping structure 20. The track 60 may be any length and have other features, such as junctions, turns, angles, or terminating ends. The track 60 may connect to a medical sterilization tray (FIG. 7) with any number of fasteners or retaining devices, many of which are well-known in the art.

The depressible arm 50, which is connected to the rail 40, and the first quantity of ratchet teeth 52, which are formed on the depressible arm 50 are components of the ratchet system which controls movement of the rail 40 relative the track 60. The ratchet system also includes the second quantity of ratchet teeth 62 formed on the track 60. Together, the depressible arm 50 and the first and second quantity of ratchet teeth 52, 62 allow for the apparatus 10 to be moved along the track 60 and retained in a stationary position along the track 60. The depressible arm 50 may be integrally formed with the rail 40 and extend away from the rail 40, as is shown in FIG. 1. The first quantity of ratchet teeth 52 may be positioned on the depressible arm 50 along the side of the depressible arm 50 that is proximate to the location of the second quantity of ratchet teeth 62. As is shown in FIG. 1, the second quantity of ratchet teeth 62 are positioned on the upper edge of the track 60 and the first quantity of ratchet teeth 52 are positioned on the top side of the depressible arm 50.

Figure 2:
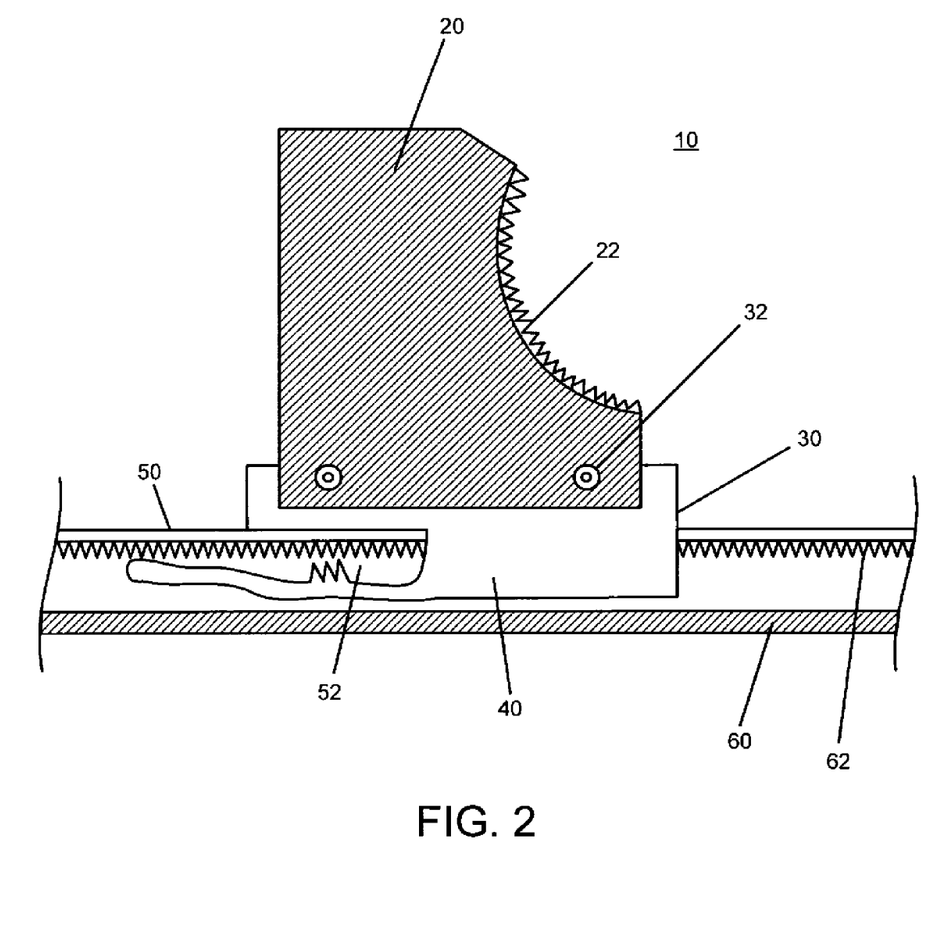
FIG. 2 is a side cross-sectional view illustration of a movable instrument holding apparatus in a disengaged position, in accordance with a first exemplary embodiment of the present disclosure.

FIG. 2 is a side cross-sectional view illustration of a movable instrument holding apparatus 10 in a disengaged position, in accordance with a first exemplary embodiment of the present disclosure. The depressible arm 50 is biasable, such that the depressible arm 50 may be moved when a force is applied thereto. In use, the depressible arm 50 may have a natural position (first position) with the first quantity of ratchet teeth 52 engaging with the second quantity of ratchet teeth 62 when no force is applied to the depressible arm 50, as is shown in FIG. 1. When the depressible arm 50 is in the first position, at least a portion of it, such as a terminating end of the depressible arm 50, may be located above a top surface of the track 60. When a force is applied to the depressible arm 50, the depressible arm 50 may be moved away from the second quantity of ratchet teeth 62 to a second position, thereby disengaging the first quantity of ratchet teeth 52 from the second quantity of ratchet teeth 62, as is shown in FIG. 2. When the first and second quantity of ratchet teeth 52, 62 are in the disengaged position, the rail 40 may be movable along the length of the track 60. Accordingly, the rail 40 may be moved along any point of the track 60 when the first and second quantities of ratchet teeth 52, 62 are disengaged, and be retained in a stationary position when the first and second quantities of ratchet teeth 52, 62 are engaged.

It is noted that the ratchet system may be controlled, at least in part, based on the shape of the first and second quantities of ratchet teeth 52, 62. For example, depending on the shape of the first and second quantities of ratchet teeth 52, 62, the rail 40 may be movable in only one direction within the track 60, or in two directions within the track 60. When one or both of the first and second quantities of ratchet teeth 52, 62 are shaped with a vertical tooth side, the rail 40 may be movable in one direction along the track 60, whereas when at least one of the first and second quantities of ratchet teeth 52, 62 have two angular teeth sides, the rail 40 may be movable in two directions along the track 60. The use of different shaped ratchet teeth within ratchet systems to allow for movement using the ratchet system is well-known in the art and does not warrant discussion herein.

In use, the apparatus 10 may allow for convenient support of a medical instrument before, after, and during a sterilization process. Since any quantity of track 60 may be used in any position(s) on the sterilization tray, the gripping structures 20 retained by the housing structure 30 and rail 40 may be positioned in a variety of locations along the sterilization tray. This ability for flexibility in locating the gripping structures 20 means that the gripping structures 20 can be quickly located or relocated to support a specific medical instrument. Thus, a medical technician simply needs to depress the depressible arm 50 to allow the rail 40 to move within the track 60 to the desired position for the gripping structure 20 to be moved to its desired holding position. Any number of gripping structures 20 may be used with any number of housing structures 30 and rails 40, thereby providing a modular system for universally accommodating a large variety of medical instruments.

FIG. 3 is a front view illustration of the rail 40, housing structure 30, and gripping structure 20 of the movable instrument holding apparatus 10 of FIG. 1, in accordance with the first exemplary embodiment of the present disclosure. The rail 40 may be formed as an inverted T-shape, generally formed from a lower portion 42 that is wider than an upper portion 44. The depressible arm 50 (FIGS. 1-2) may be connected to the lower portion 42 of the rail 40. While the housing structure 30 is shown in FIG. 3 as being wider than the upper portion 44 of the rail 40, it is noted that the housing structure 30 may have any dimension, including wider or thinner than any part of the rail 40.

Figure 4:
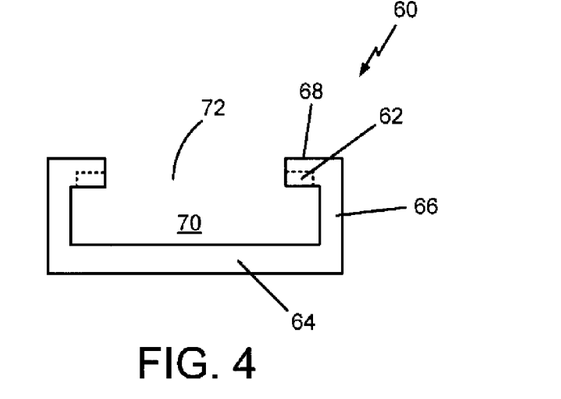
FIG. 4 is a front view illustration of the track of the movable instrument holding apparatus of FIG. 1, in accordance with the first exemplary embodiment of the present disclosure.

FIG. 4 is a front view illustration of the track 60 of the movable instrument holding apparatus 10 of FIG. 1, in accordance with the first exemplary embodiment of the present disclosure. FIG. 5 is a top view illustration of the track 60 of the movable instrument holding apparatus 10 of FIG. 1, in accordance with the first exemplary embodiment of the present disclosure. Relative to FIGS. 4-5, the track 60 may be formed from a base 64 having a plurality of walls 66 extending therefrom. At the distal ends of the plurality of walls 66 may be a lip 68, integrally connected with the wall 66. A channel 70 may be formed interior of the base 64, the walls 66, and the lips 68. The channel 70 is accessible from an open slot 72, which is located at a top of the channel 70 proximate to or between the lips 68 of each of the plurality of walls 66. The channel 70 may be sized to receive the lower portion 42 (FIG. 3) of the rail (FIG. 3). As can be seen in FIG. 4, the second quantity of ratchet teeth 62 may be positioned on an interior side of at least a portion of the lips 68, i.e., facing towards the channel 70, of each of the plurality of walls 66.

FIG. 6 is a front view illustration of the movable instrument holding apparatus 10 of FIG. 1, in accordance with the first exemplary embodiment of the present disclosure. As can be seen, the lower portion 42 of the rail 40 is sized to fit within the channel 70 of the track 60 with appropriate tolerances to allow the rail 40 to move within the track 60 along the length of the track 60. The lips 68 of the track 60 may extend towards the upper portion 44 of the rail 40, thereby preventing the rail 40 from being removed from the track 60, with the exception of removing the rail 40 from the track 60 by moving it out an open end of the track 60 (not shown). Accordingly, the upper portion 44 of the rail 40 may be positioned within the open slot 72 of the channel 70. A width of the open slot 72 may be greater than a width of the upper portion 44 of the rail 40 positioned within the open slot 72 of the channel 70 and less than a width of the lower portion 42 of the rail 40.

The second quantity of ratchet teeth 62 may be positioned on the lip 68 of the track 60, as is shown, or on another location along the track 60. For example, the second quantity of ratchet teeth 62 may be positioned along a sidewall 66 of the track 60 or a base 64 of the track 60, so long as the rail 40 is movable within the track 60 and the first quantity of ratchet teeth 52 can engage with the second quantity of ratchet teeth 62. Many variations on the positioning of the ratchet system are available, all of which are considered within the scope of the present disclosure.

Figure 7:
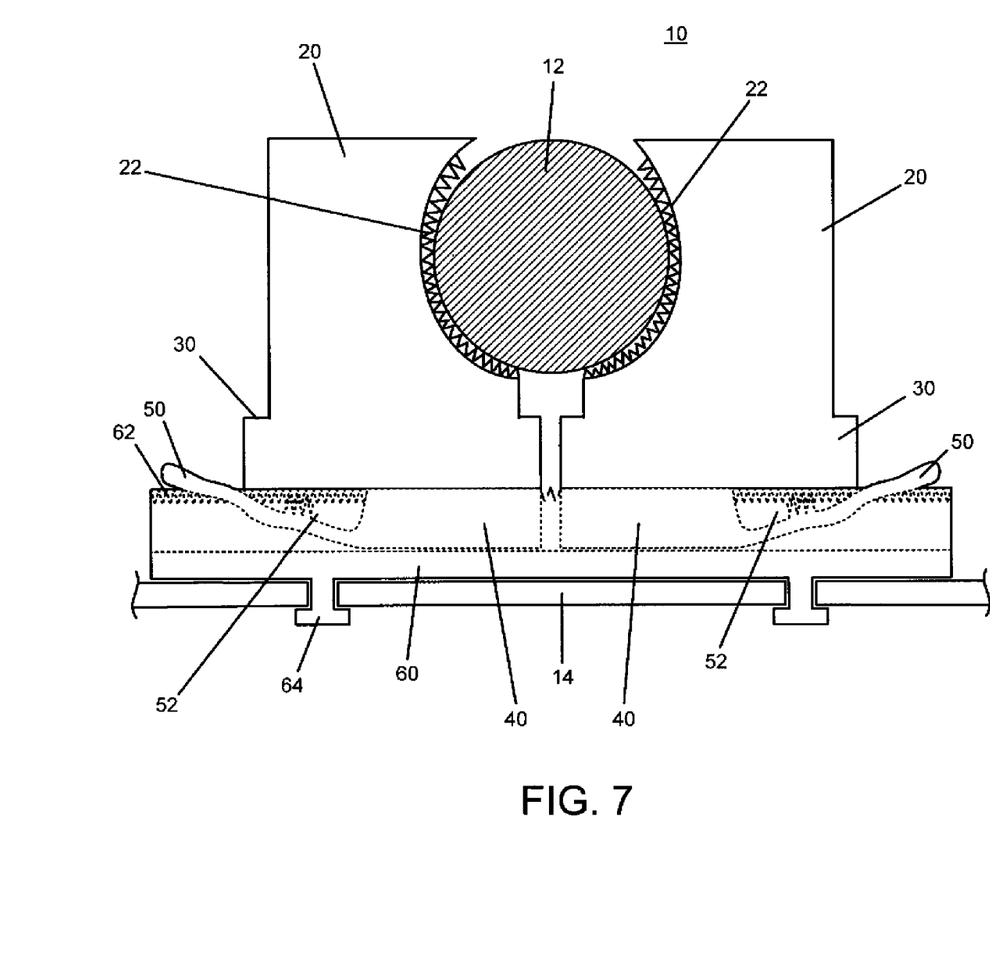
FIG. 7 is a side cross-sectional view illustration of the movable instrument holding apparatus of FIG. 1 in use with a medical instrument, in accordance with the first exemplary embodiment of the present disclosure.

FIG. 7 is a side cross-sectional view illustration of the movable instrument holding apparatus 10 of FIG. 1 in use with a medical instrument 12, in accordance with the first exemplary embodiment of the present disclosure. The apparatus 10 of FIG. 3 is substantially similar to the apparatus 10 of FIG. 1 and depicts two gripping structures 20 being used to retain a medical instrument 12, which may be understood as a system of retaining a medical instrument. The gripping structures 20, which are supported by the housing structures 30 and rails 40, respectively, may be positioned along any length of the track 60. For example, the medical instrument 12 may be positioned between two gripping structures 20 that are moved proximate to one another, such that the protrusions 22 on the gripping structures 20 contact the sides of the medical instrument 12 and frictionally contact and retain it in a stationary position. Shown in broken lines, the first and second quantities of ratchet teeth 52, 62 may be engaged to retain the gripping structures 20 in the stationary position. When the gripping structures 20 require relocating, the depressible arms 50 may be biased, thereby releasing the first and second quantities of ratchet teeth 52, 62.

Also shown in FIG. 7 is a fastener 64 which may be used to retain the track 60 to the sterilization tray 14. For example, the sterilization tray 14 may include holes that the fasteners 64 may be positioned through. The fasteners 64 may include biasable ends which compress inwards when they're being forced through the holes in the sterilization tray 14, and subsequently expand outwards when they are located outside of the holes. In this fashion, the fasteners 64 may be removably positioned to readjust and relocate the track 60, yet retain the track 60 in a stationary position on the sterilization tray 14 when they're engaged with the sterilization tray 14.

Figure 8:
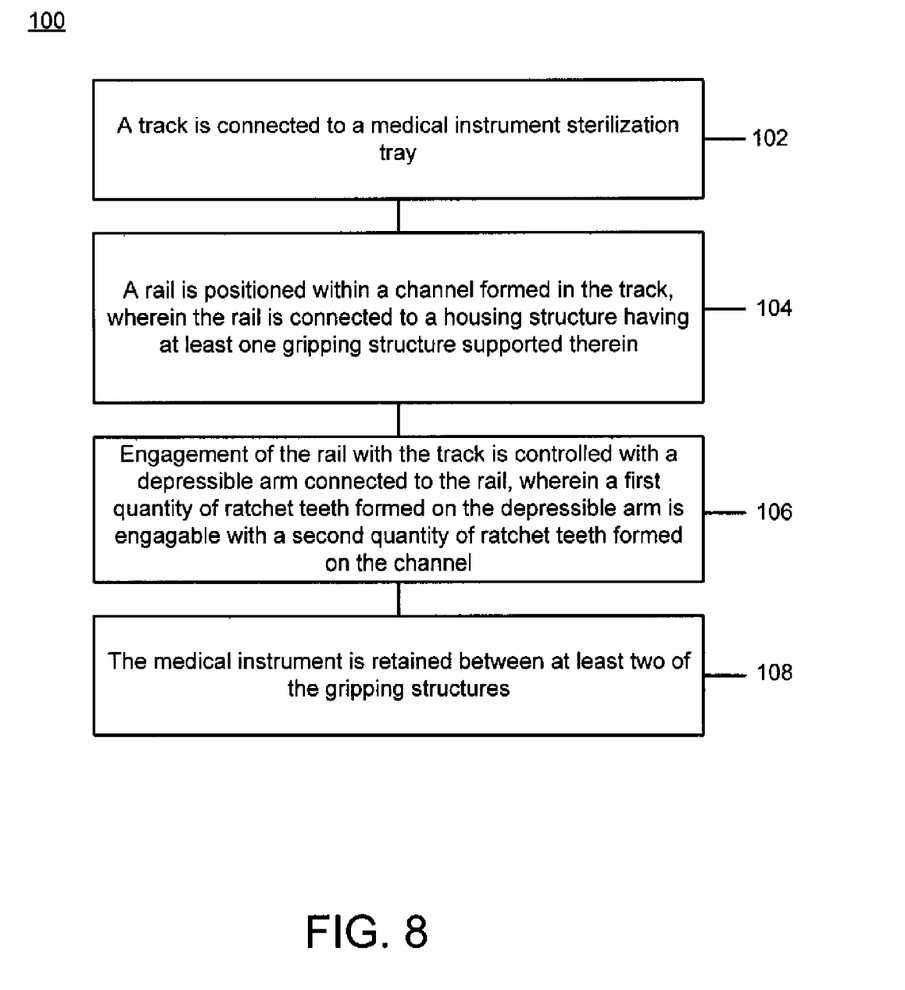
FIG. 8 is a flowchart illustrating a method of retaining a medical instrument with a movable instrument holder, in accordance with a second exemplary embodiment of the disclosure.

FIG. 8 is a flowchart 100 illustrating a method of retaining a medical instrument with a movable instrument holder, in accordance with a second exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 102, a track is connected to a medical instrument sterilization tray. A rail is positioned within a channel formed in the track, wherein the rail is connected to a housing structure having at least one gripping structure supported therein (block 104). Engagement of the rail with the track is controlled with a depressible arm connected to the rail, wherein a first quantity of ratchet teeth formed on the depressible arm is engagable with a second quantity of ratchet teeth formed on the channel (block 106). The medical instrument is retained between at least two of the gripping structures (block 108).

The method may include any number of additional steps, variations of steps, functions, or structures, including any that are disclosed relative to any embodiment of this disclosure. For example, the step of controlling engagement of the rail with the track with the depressible arm may include positioning the depressible arm in a first position to engage the first quantity of ratchet teeth with the second quantity of ratchet teeth, and positioning the depressible arm in a second position to disengage the first quantity of ratchet teeth from the second quantity of ratchet teeth. When the medical instrument is retained between the at least two gripping structures, it may be subjected to a sterilization environment or sterilization process, such as an autoclave.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claim.

What is claimed is:

1. A method of retaining a medical instrument with a movable instrument holder, the method comprising the steps of:
    connecting a track to a medical instrument sterilization tray;
    positioning a rail within a channel formed in the track, wherein the rail is connected to a housing structure having at least one gripping structure supported therein;
    controlling engagement of the rail with the track with a depressible arm connected to the rail, wherein a first quantity of ratchet teeth formed on the depressible arm is engagable with a second quantity of ratchet teeth formed on the channel; and
    retaining the medical instrument between at least two of the gripping structures.

2. The method of claim 1, wherein the step of controlling engagement of the rail with the track with the depressible arm further comprises:
    positioning the depressible arm in a first position to engage the first quantity of ratchet teeth with the second quantity of ratchet teeth; and
    positioning the depressible arm in a second position to disengage the first quantity of ratchet teeth from the second quantity of ratchet teeth.

3. The method of claim 2, further comprising the step of subjecting the medical instrument retained between the at least two gripping structures to a sterilization environment.

* * * * *